(12) United States Patent
Isch et al.

(10) Patent No.: US 9,950,106 B2
(45) Date of Patent: Apr. 24, 2018

(54) ANTIMICROBIAL BARRIER DEVICE

(71) Applicant: Cook Medical Technologies LLC, Bloomington, IN (US)

(72) Inventors: Andrew P. Isch, West Lafayette, IN (US); Steven J. Charlebois, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 188 days.

(21) Appl. No.: 14/094,182

(22) Filed: Dec. 2, 2013

(65) Prior Publication Data

US 2014/0155844 A1 Jun. 5, 2014

Related U.S. Application Data

(60) Provisional application No. 61/733,748, filed on Dec. 5, 2012.

(51) Int. Cl.
| | |
|---|---|
| *A61L 29/00* | (2006.01) |
| *A61M 5/00* | (2006.01) |
| *A61M 39/16* | (2006.01) |
| *A61M 39/18* | (2006.01) |
| *A61M 25/00* | (2006.01) |
| *A61L 31/06* | (2006.01) |
| *A61L 31/16* | (2006.01) |
| *A61M 25/02* | (2006.01) |

(52) U.S. Cl.
CPC ............ *A61M 5/001* (2013.01); *A61L 31/06* (2013.01); *A61L 31/16* (2013.01); *A61M 25/00* (2013.01); *A61M 39/16* (2013.01); *A61M 39/18* (2013.01); *A61L 2300/202* (2013.01); *A61L 2300/206* (2013.01); *A61L 2300/404* (2013.01); *A61L 2300/406* (2013.01); *A61M 2025/0056* (2013.01); *A61M 2025/0273* (2013.01)

(58) Field of Classification Search
CPC ..................................................... A61L 29/00
See application file for complete search history.

(56) References Cited

U.S. PATENT DOCUMENTS

| | | | |
|---|---|---|---|
| 3,683,911 | A | 8/1972 | McCormick |
| 4,040,427 | A | 8/1977 | Winnie |
| 4,380,234 | A | 4/1983 | Kamen |
| 4,915,694 | A | 4/1990 | Yamamoto et al. |
| 5,236,421 | A | 8/1993 | Becher |
| 5,447,492 | A | 9/1995 | Cartmell et al. |
| 5,620,424 | A | 4/1997 | Abramson |

(Continued)

OTHER PUBLICATIONS

Brochure: "Anti-Infection—StrataNF™ Silicone Foley Catheter with Comfort Layered Technology," *Rochester Medical Corporation*, Stewartville, MN, 2005, 12 pages.

(Continued)

*Primary Examiner* — Benjamin Packard
(74) *Attorney, Agent, or Firm* — Brinks Gilson & Lione (57) ABSTRACT

The invention relates to an antimicrobial barrier device and methods of manufacture. The antimicrobial barrier comprises one or more antimicrobial drugs that inhibit biofilm formation and bacterial and/or fungal growth. The antimicrobial barrier is suited for use with insertable devices (e.g., catheters) to reduce the incidence of infection at and around the insertion site.

20 Claims, 3 Drawing Sheets

(56) References Cited

U.S. PATENT DOCUMENTS

| | | | |
|---|---|---|---|
| 5,665,477 | A | 9/1997 | Meathrel et al. |
| 6,083,208 | A * | 7/2000 | Modak .................. A61L 27/34 424/422 |
| 6,165,168 | A * | 12/2000 | Russo ................. A61M 39/045 604/247 |
| 6,863,674 | B2 | 3/2005 | Kasahara et al. |
| 7,363,091 | B1 | 4/2008 | Chen et al. |
| 7,993,670 | B2 | 8/2011 | Simonson et al. |
| 8,025,658 | B2 | 9/2011 | Chong et al. |
| 2002/0193879 | A1* | 12/2002 | Seder ...................... A61F 2/203 623/9 |
| 2004/0219195 | A1 | 11/2004 | Hart et al. |
| 2007/0225652 | A1 | 9/2007 | Scherr |
| 2007/0299409 | A1 | 12/2007 | Whitbourne et al. |
| 2008/0145446 | A1* | 6/2008 | Johnson ................. A01N 25/34 424/601 |
| 2009/0157000 | A1 | 6/2009 | Waller |
| 2009/0215924 | A1* | 8/2009 | Zhu ........................ A01N 25/04 523/122 |
| 2010/0076362 | A1* | 3/2010 | Utterberg ................ A61F 13/02 602/43 |
| 2010/0318052 | A1* | 12/2010 | Ha .......................... A61F 13/02 604/385.01 |
| 2012/0130315 | A1 | 5/2012 | Weadock et al. |

OTHER PUBLICATIONS

Berrington, A.; et al. "Use of Antibiotic Locks to Treat Colonized Central Venous Catheters," *J. Antimicrobial Chemotherapy*, 2001, 48, 597-603.

Bouza, E.; et al. "A Randomized and Prospective Study of 3 Procedures for the Diagnosis of Catheter-Related Bloodstream Infection Without Catheter Withdrawal," *CID*, 2007, 44, 820-826.

Darouiche, R.O.; et al. "A Comparison of Two Antimicrobial-Impregnated Central Venous Catheters," *N. Eng. J. Med.*, 1999, 340, 1-8.

Donlan, R.M. "Biofilms and Device-Associated Infections," *Emerging Infectious Diseases*, 2001, 7, 277-281.

Donlan, R.M. "Biofilm Elimination on Intravascular Catheters: Important Considerations for the Infectious Disease Practitioner," *CID*, 2011, 52, 1038-1045.

Jacobsen, et al. "Complicated Catheter-Associated Urinary Tract Infections Due to *Escherichia coli* and *Proteus mirabilis*," *Clin. Microbiology Rev.*, 2008, 21, 26-59.

Mashak, A.; et al. "Silicone Polymers in Controlled Drug Delivery Systems: A Review," *Iranian Polymer J.*, 2009, 18, 279-295.

Newman, D.K. "Prevention and Management of Catheter-Associated UTIs," *Inf. Dis. Special Ed.*, 2010, 13-20.

Nicolle, L.E.; et al. "Infectious Diseases Society of America Guidelines for the Diagnosis and Treatment of Asymptomatic Bacteriuria in Adults," *CID*, 2005, 40, 643-654.

O'Grady, N.P.; et al. "Guidelines for the Prevention of Intravascular Catheter-Related Infections," *CID*, 2011, 52, e1-e32.

Stickler, D.J. "Bacterial Biofilms in Patients with Indwelling Urinary Catheters," *Nature Clin. Prac. Urology*, 2008, 5, 598-608.

Trautner, B.W.; et al. "Role of Biofilm in Catheter-Associated Urinary Tract Infection," *Am. J. Infect. Control.*, 2004, 32, 177-183.

Website: www.medicaldesignbriefs.com_component_content_article_12817, 2012, 2 pages.

Website: www.medicaldesignbriefs.com_component_content_article_12817_start=1, 2012, 2 pages.

* cited by examiner

ANTIMICROBIAL BARRIER DEVICE

RELATED APPLICATIONS

The present patent document claims the benefit of the filing date under 35 U.S.C. § 119(e) of Provisional U.S. Patent Application Ser. No. 61/733,748, filed Dec. 5, 2012, which is hereby incorporated by reference.

TECHNICAL FIELD

The present invention relates to an antimicrobial barrier device for use in reducing the incidence of infection in a medical treatment area. The antimicrobial barrier device comprises drug agents that inhibit biofilm formation, elute from the barrier device, and inhibit infection of the treatment site.

BACKGROUND OF THE INVENTION

The prolonged placement of insertable medical devices, such as needles and catheters, presents the risk of infection from bacteria and fungi at the site of insertion. Infection can result from the colonization of the insertion site by microorganisms present on the skin. The microorganisms can migrate into a patient's body along the outer surface of the insertable medical device resulting in infection.

The risk of infection is common with the use of urinary catheters for draining bodily fluids. Untreated infections can lead to infection of the kidneys. Infection typically results from manipulation of the catheter and drainage device. Virtually all patients undergoing long term urinary catheterization can develop bacteriurea. See Nicolle et al. *Clin. Infect. Dis.* (2005) 40(5), 643-654. Attempts to prevent urinary tract infection from long-term catheterization have produced mixed results. Jacobsen et al. *Clin. Microbiol. Rev.* (2008) 21, 26-59. Coating a catheter with an antimicrobial solution or lubricant has not proven successful. Limited trials with antibiotic-impregnated catheters, however, produced some benefit.

Infections can also result from the use of percutaneously inserted catheters and i.v. tubes. Catheter-related infections represent a significant proportion of hospital acquired infection and contribute to increased morbidity and mortality. Bouza et al. *Clin. Infect. Dis.* (2007) 44 (6), 820-26. General guidelines for prevention of infection include cleaning the area of insertion with an antiseptic such as 70% alcohol, tincture of iodine, or chlorhexidine. O'Grady et al. *Clin. Infect. Dis.* (2011) 52, pp. e1-e32. In spite of these preventive measures, prolonged placement of catheters can nonetheless result in infection.

Long term use of intravascular and urinary catheters is associated with the possibility of biofilm formation on the catheter. Microorganisms on the skin of a patient around a catheter insertion site can attach to the external surface and form a biofilm. Donlan, R. *Clinical Infectious Diseases* (2011) 52, 1038-1045; Trautner et al. *Am. J. Infect. Control.* (2004) 32, 177-183. Biofilms are microbial communities that colonize the surface to which they are attached and produce a gel-like extracellular polymeric substance matrix. Once established, organisms living in a biofilm can become much more resistant to antimicrobial agents than planktonic (i.e., freely suspended) organisms. Biofilms can also serve as a source of microorganisms that can subsequently infect a patient. Newman, D. *Infectious Diseases Special Edition* (2010) 13-20.

Current techniques used to impregnate drugs into materials to create drug eluting devices are limited in how much drug can be imbibed into the material. Current methods also require a large amount of drug to be unused and wasted during the imbibement process. Another drawback of using current imbibement/impregnation techniques is that drugs can elute more quickly than desired, thus decreasing the useful lifetime of the device.

Therefore, a need exists for novel devices and methods for preventing and reducing the incidence of infection at the site of insertion of an insertable medical device and inhibiting biofilm formation, particularly in the case of prolonged placement of a catheter.

SUMMARY OF THE INVENTION

The present invention relates to an antimicrobial barrier device for use in conjunction with an insertable medical device such as a catheter or needle. The invention also relates to kits comprising the antimicrobial barrier device and methods of manufacture thereof.

A first aspect of the invention relates to an antimicrobial barrier device comprising a soft durometer silicone body, incorporated within which is one or more antimicrobial drugs, wherein the soft durometer silicone body is substantially resistant to microbial colonization, has a first surface adapted to conform to a treatment area of a patient and has a hole extending through the soft durometer silicone body that is adapted to receive and seal to an insertable medical device.

A second aspect of the invention relates to kits including an insertable medical device and an antimicrobial barrier device.

A third aspect of the invention relates to a method of manufacturing an antimicrobial barrier device.

DETAILED DESCRIPTION

Definitions

"Antimicrobial," as used herein, refers to the general property to inhibit the growth of, or kill, bacteria and/or fungi.

"Antimicrobial barrier disc" as used herein, refers to an antimicrobial barrier device having a greater width than thickness. The "disc" of the "antimicrobial barrier disc" may have different shapes (e.g., round, square, triangular, tabbed, etc.) and may be relatively flat or dome-shaped (i.e., concave on the first surface) or saddle-shaped (i.e., convex on the first surface).

"Soft durometer silicone" refers to silicone having a Shore durometer on the "A" scale of about 10 to about 80 (i.e., about 10 A to about 80 A).

Figures 1A, 1B:
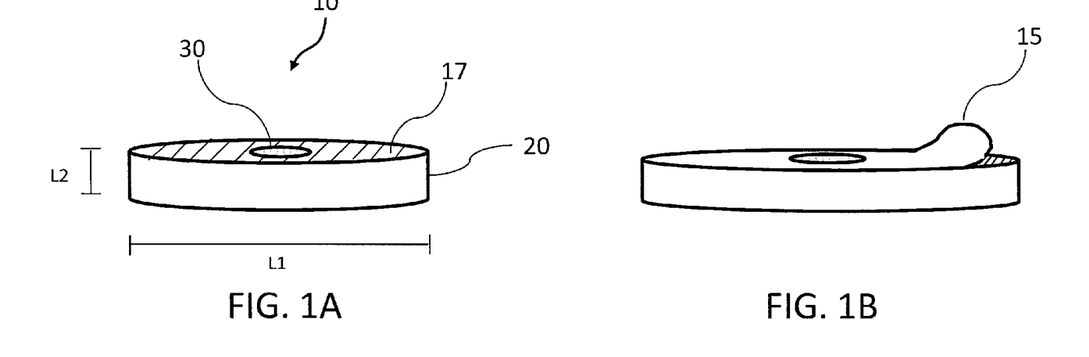
FIG. 1A is a perspective view of one embodiment of the antimicrobial barrier device.
FIG. 1B is a perspective view of one embodiment of the antimicrobial barrier device showing an optional peel-away layer.

Referring to FIG. 1A, which shows one embodiment of the invention, an antimicrobial barrier 10 comprises a soft durometer silicone body 20. In one embodiment, the silicone body is about 10 A-80 A durometer. In another embodiment, the silicone body is about 10 A-50 A durometer. In still another embodiment, the silicone body is about 50 A durometer. A silicone body of about 50 A durometer can have a range of durometers with a minimum 40 A or between 45 A-55 A depending on the method of manufacture employed. The soft durometer silicone body can be made using low-consistency or high-consistency silicone elastomers available from NuSil Technologies, LLC (e.g., MED-6215, MED-4050).

Figure 1C:
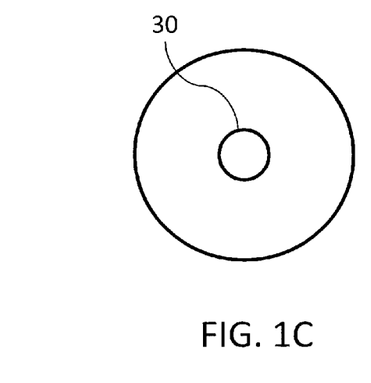
FIG. 1C is a top view of an embodiment of the antimicrobial barrier device.
Figure 1D:
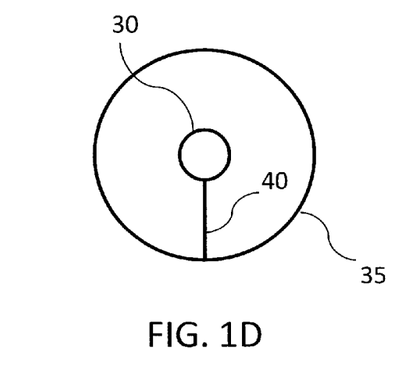
FIG. 1D is a top view of an embodiment of the antimicrobial barrier device with a slit.

As shown in FIGS. 1A, 1C, and 1D, a hole 30 extends through the body 20 of the antimicrobial barrier device to accommodate an insertable medical device. Depending on the application, the size and shape of the hole can vary with the size of the insertable medical device. Preferrably, the size of the hole is equal to or smaller than the circumference of the insertable medical device. In certain embodiments, the hole is substantially round or rounded. In other embodiments, the hole is a scalloped oval or ellipse. This configuration allows the insertable medical device to be inserted at an angle and not buckle the surface of the disc.

Figure 1E:
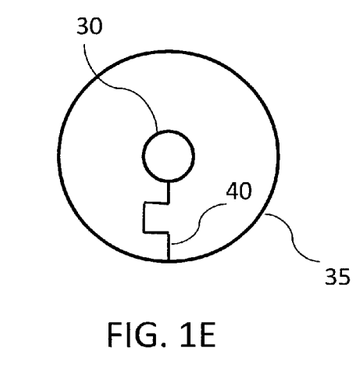
FIG. 1E is a top view of an embodiment of the antimicrobial barrier device with a step-shaped slit.

Optionally, the soft durometer silicone body 20 has a slit 40 which extends from the outer edge 35 of the silicone body to the hole 30. The slit is adapted to permit placement of the antimicrobial barrier around a catheter that has already been inserted into a patient. Although slit 40 is shown as a straight line in FIG. 1D, it may also be curved, or have a step shape as in FIG. 1E.

The antimicrobial barrier 10 has a first surface 17, adapted to conform to a patient's skin (i.e., a treatment area). The barrier device 10 is shaped to allow the first surface 17 to maintain efficient contact with a patient's skin. The antimicrobial barrier may be a relatively flat as shown in the rounded antimicrobial barrier disc embodiment in FIG. 1A. In other embodiments, the antimicrobial barrier disc may be oval, square, triangular, or have some other geometric shape adapted to make efficient contact with a patient's skin. Alternatively, the disc may be cup- or dome-shaped such that the antimicrobial barrier has a concave surface on the skin side. In either case, the antimicrobial barrier is generally greater in width than thickness, as shown, respectively, by dimensions L1 and L2. In one embodiment, the antimicrobial barrier is a small disc approximately the size and shape (diameter and thickness) of a dime to a quarter. In another embodiment, the antimicrobial barrier has one or more wings or tabs around the perimeter (i.e., tab-shaped), which allow it to be affixed to a patient's skin, for example, by taping down, tying, or suturing, depending on the application. The wings may be formed from soft durometer silicone or other compatible material.

The invention also provides means for adhering the antimicrobial barrier to the skin of a patient. Means for adhering the antimicrobial barrier include an adhesive, tape, bandages, ties, sutures, or other means well known in the medical arts. For example, the antimicrobial barrier of the invention may optionally have an adhesive material applied to the "skin" side (i.e., the first surface 17). The adhesive may be a hydrogel-type adhesive. Other adhesives suitable for use with the invention include medical grade, pressure-sensitive adhesives, such as acrylic adhesives, acrylate ester/vinyl pyrrolidone copolymers, dimethyl silicone polymers, acrylate polymers, polyisobutylenes, and polybutylenes. See Venkatraman et al., *Biomaterials* (1998) 19, 1119-1136. FIG. 1B illustrates an embodiment of the invention that provides a peel-away layer 15 to protect an adhesive on the first surface 17. Use of an adhesive is particularly suitable in the embodiments shown in FIGS. 1D and 1E having a slit as described above.

Alternatively, the antimicrobial barrier may have straps adapted to wrap around a body structure such as an arm or leg and hold the barrier device against the skin. The straps, in turn, may be joined with tape or Velcro to allow the straps to maintain a firm grip around the body structure.

The antimicrobial barrier comprises an antibacterial and/or antifungal drug that can inhibit microbial colonization and biofilm formation. Antibacterial drugs that may be used with the present invention include, but are not limited to, rifamycins such as rifampicin; nitrofurantoin; triclosan; trimethoprim; nalidixic acid; vancomycin; tetracyclines such as doxycycline, minocycline, and tetracycline; aminoglycosides such as amikacin, gentamicin, neomycin, and tobramycin; and fluoroquinolone drugs such as ciprofloxacin, levofloxacin, trovafloxacin, and gemifloxacin. Antifungal drugs for use with the invention include, but are not limited to, gentian violet, flucytosine, and azole drugs, such as fluconazole, miconazole, itraconazole, ketoconazole, and clotrimazole. Chlorhexidine may also be used with the present invention. Combinations of the foregoing antimicrobial agents may also be used together in the antimicrobial barrier of the present invention; for example, the "Gendine" combination of gentian violet and chlorhexidine. Other combinations include, but are not limited to minocycline with fluconazole, gentian violet with ciprofloxacin, triclosan with fluconazole, and trimethoprim with levofloxacin. More than one antibacterial drug may be directly incorporated into the silicone body either with or without one or more antifungal drugs. The foregoing list of antimicrobial drugs is merely exemplary and is not intended to limit the scope of antimicrobial agents that may be directly incorporated into the antimicrobial barrier device.

The amount of mg of drug directly incorporated per gram of silicone body (mg/g) varies with the drug and the particular application. In general, however, the antimicrobial barriers of the invention have much greater concentrations of antimicrobial drug than devices manufactured by impregnation techniques. In some embodiments, one or more antimicrobial drugs is directly incorporated each in amounts of about 1 mg/g to about 30 mg/g. In other embodiments, one or more antifungal drugs is directly incorporated each in amounts of about 1 mg/g to about 20 mg/g. In other embodiments, about 1 mg/g to about 30 mg/g of one or more antibacterial drugs is each directly incorporated into the silicone body. In other embodiments, about 1 mg/g to about 30 mg/g each of one or more antibacterial drugs and about 1 mg/g to about 20 mg/g each of one or more antifungal drugs is directly incorporated into the silicone body. In still other embodiments, about 10 mg/g to about 20 mg/g to about 30 mg/g of ciprofloxacin is directly incorporated into the silicone body, optionally with about 1 mg/g to about 20 mg/g each of one or more antifungal drugs such as, but not limited to, fluconazole, itraconazole, and gentian violet. In still other embodiments, about 20 mg/g of ciprofloxacin is directly incorporated with about 1 mg/g to about 6 mg/g each of one or more of fluconazole, itraconazole, or gentian violet. In still other embodiments, about 4 mg/g to about 20 mg/g to about 30 mg/g of levofloxacin is directly incorporated into the silicone body, optionally with about 1 mg/g to about 20 mg/g each of one or more antifungal drugs such as, but not limited to, fluconazole, itraconazole, and gentian violet. In still other embodiments, about 20 mg/g of levofloxacin is directly incorporated with about 1 mg/g to about 6 mg/g each of one or more of fluconazole, itraconazole, or gentian violet. In still other embodiments, about 5 mg/g to about 20 mg/g to about 30 mg/g of minocycline or its hydrochloride salt is directly incorporated into the silicone body, optionally with about 1 mg/g to about 20 mg/g each of one or more antifungal drugs such as, but not limited to, fluconazole, itraconazole, and gentian violet. In still other embodiments, about 20 mg/g to about 26 mg/g of minocycline or its hydrochloride salt is directly incorporated with about 1 mg/g to about 6 mg/g each of one or more of fluconazole, itraconazole, or gentian violet. In still other embodiments, about 2 mg/g to about 10 mg/g to about 20 mg/g of triclosan is directly incorporated into the silicone body, optionally with about 1 mg/g to about 20 mg/g each of one or more antifungal drugs such as, but not limited to, fluconazole, itraconazole, and gentian violet. In still other embodiments, about 10 mg/g to about 20 mg/g of triclosan is directly incorporated with about 1 mg/g to about 6 mg/g each of one or more of fluconazole, itraconazole, or gentian violet. In still other embodiments, about 2 mg/g to about 10 mg/g to about 20 mg/g of trimethoprim is directly incorporated into the silicone body, optionally with about 1 mg/g to about 20 mg/g each of one or more antifungal drugs such as, but not limited to, fluconazole, itraconazole, and gentian violet. In still other embodiments, about 5 mg/g to about 12 mg/g of trimethoprim is directly incorporated with about 1 mg/g to about 6 mg/g each of one or more of fluconazole, itraconazole, or gentian violet.

Multiple antibiotics may be incorporated into the silicone body, either with or without an antifungal agent. For example, in certain embodiments, about 2 mg/g to about 10 mg/g to about 20 mg/g of trimethoprim with about 4 mg/g to about 20 mg/g to about 30 mg/g of levofloxacin is directly incorporated into the silicone body, optionally with about 1 mg/g to about 20 mg/g of an antifungal drug such as, but not limited to, fluconazole, itraconazole, and gentian violet. In still other embodiments, about 5 mg/g to about 12 mg/g of trimethoprim and about 4 mg/g to about 10 mg/g of levofloxacin is directly incorporated with about 1 mg/g to about 6 mg/g of fluconazole, itraconazole, or gentian violet.

Exemplary amounts of drug are provided in the table below.

TABLE 1

Drug Concentration in the Antimicrobial barrier Device

| Drug | Amount (mg/g)[a] |
|---|---|
| ciprofloxacin | 20 |
| levofloxacin | 4-30 |
| minocycline HCl | 12-26 |
| nitrofurantoin | 20 |
| trimethoprim | 5-12 |
| gentian violet | 1-4 |
| fluconazole | 1-12 |
| itraconazole | 1-6 |
| triclosan | 5-20 |

[a]mg of drug per g of the silicone body w/w.

Varying drug amounts and combinations may be directly incorporated into various grades of silicone elastomers. For example, the foregoing drugs and drug amounts may be directly incorporated into relatively soft durometer (e.g., 10 A to 50 A) silicone elastomers such as MED-6215 and MED-4050 available from NuSil. As will be explained below, antimicrobial barrier devices manufactured from these grades of silicone elastomer inhibit biofilm formation, microbial growth, and slowly elute the directly incorporated drug(s).

The antimicrobial barrier device of the invention can inhibit biofilm formation and either or both of bacterial and fungal growth. For example, the antimicrobial barrier device can inhibit the growth of bacteria such as, but not limited to, *E. coli*, *E. faecalis*, and *P. aeruginosa*. The antimicrobial barrier can also inhibit fungi such as, but not limited to *C. albicans*.

The antimicrobial barrier device can inhibit (i.e. resist) biofilm formation by bacteria such as *E. coli*, *E. faecalis*, and *P. aeruginosa*. For example, in some embodiments of the invention the antimicrobial barrier comprising directly incorporated antibacterial agent(s) (e.g., ciprofloxacin, levofloxacin) inhibits substantially all biofilm formation by the foregoing bacteria. In other embodiments, at least about 80% biofilm formation is inhibited. In other embodiments, the antimicrobial barrier comprising directly incorporated antibacterial(s) (e.g., ciprofloxacin, levofloxacin) substantially inhibits all biofilm formation after exposure of the barrier device to an artificial urine solution for 1-3 days. In still other embodiments, the antimicrobial barrier comprising directly incorporated antibacterial(s) (e.g., ciprofloxacin, levofloxacin) inhibits at least about 60% to about 80% biofilm formation after exposure of the barrier device to an artificial urine solution for 1-3 days.

Figure 2:
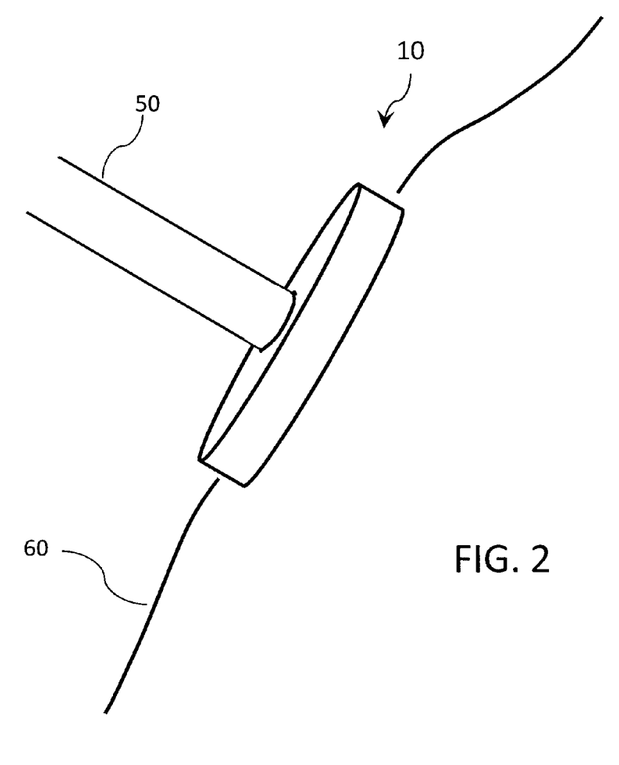
FIG. 2 is a perspective view of the antimicrobial barrier device attached to a patient and surrounding an insertable medical device.

The use of soft durometer silicone allows the barrier device to seal to an insertable medical device, such as a catheter, and conform easily to a patient's skin. FIG. 2 shows the antimicrobial barrier 10 surrounding an insertable medical device 50 and contacting a patient's skin. This arrangement leaves very little space or air for bacteria or fungi to colonize. The antimicrobial barrier device may be implemented anywhere there is an opening or insertion point in a patient, and may be applied to a number of existing products to increase safety and reduce infection.

In addition to preventing microbial colonization around an insertion point, the antimicrobial barrier device may slowly elute antimicrobial drugs to provide additional protection for the patient in the area surrounding the insertion point. Drugs may have very slow elution rates from the antimicrobial barrier device, making it active for long periods of time. This allows the antimicrobial barrier device to remain in place for extended periods of time without need for replacement. Use of a hydrogel-based adhesive may enhance drug elution.

In some embodiments of the invention, about 1% to about 15% of the antimicrobial drug (e.g., ciprofloxacin, levofloxacin) elutes after exposure to artificial urine for about 3 days. In other embodiments, less than about 10% of the antimicrobial drug (e.g., ciprofloxacin, levofloxacin) elutes after exposure to artificial urine for about 3 days.

In some embodiments of the invention, an antimicrobial barrier comprises about 1 mg/g to about 30 mg/g of an antimicrobial agent(s), elutes about 1% to about 15% of the antimicrobial agent(s) after exposure to artificial urine for about 1-3 days, and inhibits substantially all biofilm formation thereon. In other embodiments of the invention, an antimicrobial barrier comprises about 1 mg/g to about 30 mg/g of an antimicrobial agent(s), elutes about 1% to about 15% of the antimicrobial agent(s) after exposure to artificial urine for about 1-3 days, and inhibits at least about 80% biofilm formation thereon. In other embodiments of the invention, an antimicrobial barrier comprises about 1 mg/g to about 30 mg/g of an antimicrobial agent(s), and after exposure to artificial urine for about 1-3 days: (1) elutes about 1% to about 15% antimicrobial agent(s); and (2) inhibits substantially all biofilm formation thereon. In other embodiments of the invention, an antimicrobial barrier comprises about 1 mg/g to about 30 mg/g of an antimicrobial agent(s), and after exposure to artificial urine for about 1-3 days: (1) elutes about 1% to about 15% of the antimicrobial agent(s); and (2) inhibits at least about 60-80% biofilm formation thereon. In some embodiments, the antimicrobial barrier inhibits bacterial or fungal growth within about 10-30 mm of the outer edge 35 in the Zone of Inhibition (ZOI) test. In the foregoing embodiments, the soft durometer silicone body is about 10 A-80 A durometer, about 10 A-50 A durometer, or about 50 A durometer.

The insertable medical device may be a needle, an infusion set or device, a peripheral venous catheter or needle, an indwelling infusion needle, a butterfly needle, a subcutaneous access device, an insulin pump needle, a patient controlled analgesia (PCA) pump needle, an arterial catheter, a central venous catheter, a dialysis catheter, a peritoneal dialysis catheter, a nephrostomy catheter, a percutaneous cystostomy catheter, an indwelling paracentesis or pleurocentesis catheter or drain, a percutaneous nephrostomy, a cystostomy tube, a spinal or epidural catheter or a sensor.

In one aspect of using the antimicrobial barrier device, an insertable medical device (e.g., catheter) is first inserted through the hole 30 in the antimicrobial barrier before being inserted into the patient. After insertion, the antimicrobial barrier is slid down the shaft of the insertable medical device and comes to rest on the patient's skin as illustrated in FIG. 2. The antimicrobial barrier may be affixed to the patient's skin with an adhesive, by tying, taping, or with a suture, or may be allowed to rest on the skin surface at the point of catheter entry without attachment.

In the case where the antimicrobial barrier has an adhesive protected by a peel-away layer, the antimicrobial barrier is slid onto the insertable medical device before it is inserted into the patient. The insertable medical device is then inserted into the patient, the peel-away layer is removed, and the antimicrobial barrier is adhered to the patient's skin. An analogous procedure would be used where the antimicrobial barrier has one or more "wings" around the perimeter and is affixed by taping down, tying, or suturing to the patient's skin, depending on the application. The antimicrobial barrier may be removed each time a catheter needs to be replaced, or may be reused with a new catheter.

In an alternative aspect of the invention, the antimicrobial barrier is first placed on the patient's skin (with or without adhesive, taping, suturing, or tying) and the insertable medical device is passed through the antimicrobial barrier and inserted into the body.

In the case where an insertable medical device is already in place in a patient, a antimicrobial barrier device having a slit (see FIGS. 1D and 1E) may be placed around the insertable medical device, the optional peel-away cover removed, and then brought into contact with the patient's skin.

One aspect of the invention provides a kit comprising an insertable medical device and an antimicrobial barrier device as described herein. For example, in one embodiment, the kit comprises a antimicrobial barrier device and a catheter, a needle, an infusion device, a peripheral venous catheter, a peripheral venous catheter needle, an indwelling infusion needle, a butterfly needle, a subcutaneous access device, an insulin pump needle, a patient controlled analgesia pump needle, an arterial catheter, a central venous catheter, a dialysis catheter, a peritoneal dialysis catheter, a nephrostomy catheter, a percutaneous cystostomy catheter, an indwelling paracentesis or pleurocentesis catheter or drain, a percutaneous nephrostomy, a cystostomy tube, a spinal or epidural catheter or a sensor.

Methods of Manufacture.

The antimicrobial barrier device of the invention is made with one or more antimicrobial drugs before production using direct incorporation techniques. In order to decrease the amount of drug needed to create a high dose device, and not be limited by imbibement concentration gradients, a direct incorporation method has been developed where the drug is mixed into a silicone elastomer pre-polymerization, which allows one to create the barrier device with the drug-loaded material. Drugs are directly incorporated into the silicone elastomer before the material is formed and cured into the appropriate size and shape. This significantly reduces waste and can reduce manufacturing steps. Also, by placing the drug within the material pre-polymerization, drugs have slower elution rates when compared to imbibed/impregnated material.

Suitable elastomeric silicones include low-consistency silicone elastomers such as, but are not limited to, MED-6215, available from NuSil. Low consistency elastomers are pourable liquids of variable viscosities. MED-6215, for example, includes two liquid silicones with viscosities of about 90 cP and about 6,000 cP. Selected drugs are mixed first with one of the low-consistency elastomers, followed by mixing with the second low-consistency elastomer in appropriate proportions, molding, and then curing according to the manufacturer's instructions. Other suitable silicones include high-consistency elastomers such as, but not limited to, MED-4050. High-consistency elastomers have approximately the consistency of clay and selected drugs can be incorporated into high-consistency elastomers by milling the components of the elastomer system together with the drugs followed by molding and curing.

Figure 3:
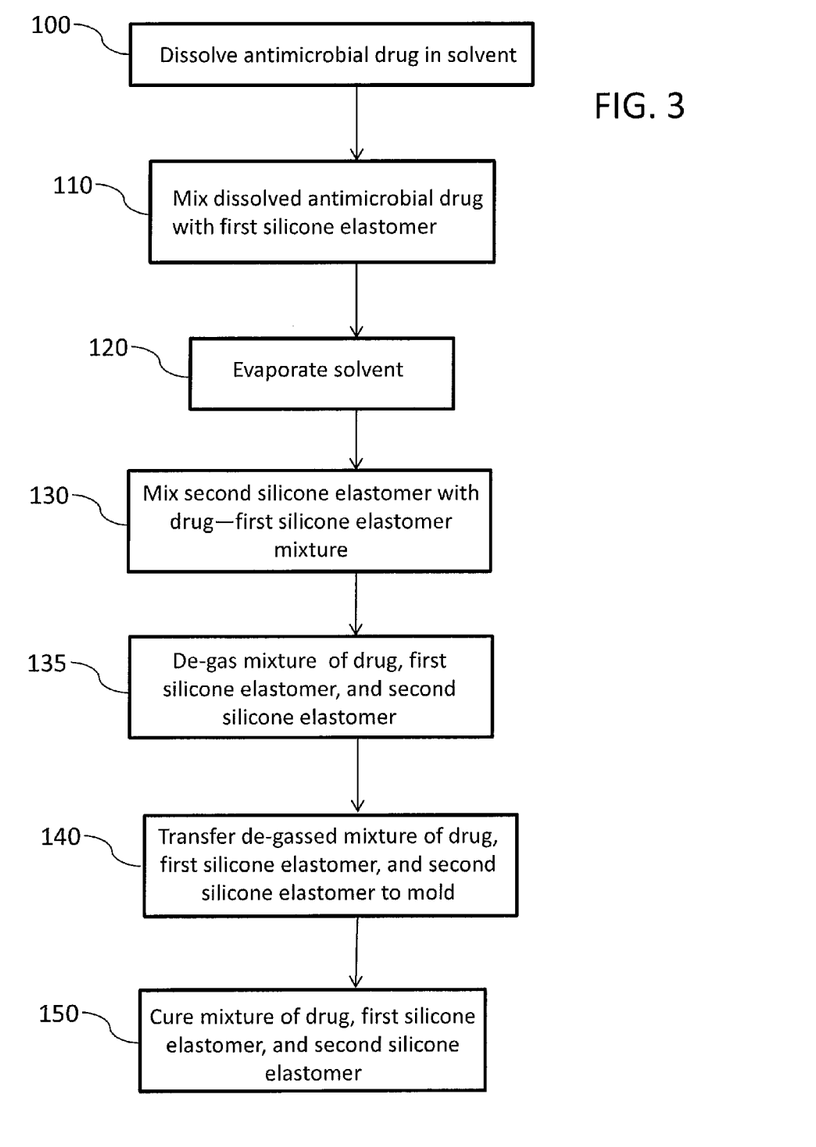
FIG. 3 shows an embodiment of the method of manufacturing a direct-incorporated antimicrobial barrier.

Referring to FIG. 3, in one embodiment of the direct incorporation method, one or more drugs is first dissolved in a suitable solvent or solvent mixture (step 100). Suitable solvents (e.g., dichloromethane, methanol, ethanol, alcohol+water) can dissolve the desired drug and also be miscible in one part of the silicone system. The amount of solvent used in each situation should be the smallest amount possible to allow for the drug to enter the silicone elastomer in a dissolved state, and be miscible in the silicone elastomer. Using this technique, the desired amount of drug can be directly incorporated into the soft durometer silicone, optionally just below the saturation point.

Following dissolution of the one or more drugs in an appropriate solvent, the drug solution is thoroughly mixed into one part of a two-part silicone elastomer system (step 110). Following evaporation of the solvent used for drug dissolution (step 120), the second part of the silicone elastomer system is mixed with the drug—first silicone elastomer mixture as specified according to the manufacturer's instructions (step 130). The material is then optionally de-gassed according to the manufacturer's instructions under vacuum until bubbling stops (step 135). De-gassing is recommended with the use of the silicone elastomer system MED-6215 from NuSil. After the optional de-gassing step, the mixture is transferred to a mold (step 140), and polymerized (i.e. cured) (step 150). For example, the silicone elastomer system MED-6215 from NuSil may be cured at room temperature, at 65° C. for 40 minutes or 100° C. for two minutes. This process gives a uniform (i.e. homogenous) distribution of drug throughout the silicone body. Use of MED-6215 silicone elastomer in this process directly incorporates a drug into an antimicrobial barrier device having about a 50 A soft durometer silicone body.

In some embodiments, the two-part silicone elastomer system comprises a first silicone elastomer of about 6000 cP (centipoise) and a second silicone elastomer of about 90 cP, where the first and second silicone elastomers are used in a ratio of about 10:1. For example, in some embodiments, the one or more antimicrobial drugs is dissolved in a solvent such as dichloromethane and the resultant solution mixed with about 10 parts of a first silicone elastomer having a viscosity of about 6000 cP. Following thorough mixing of the dissolved drug and the about 6000 cP silicone elastomer, the solvent (e.g., dichloromethane) is evaporated, thus leaving the drug homogeneously mixed with the about 6000 cP silicone elastomer. This mixture is then thoroughly mixed with about one part of a second silicone elastomer of viscosity about 90 cP and the resultant mixture de-gassed, transferred to a mold and cured under conditions appropriate for the particular one or more antimicrobial drugs.

Procedure for Directly Incorporating Minocycline and Rifampin into a 50 A Durometer Silicone Elastomer.

Minocycline (0.632 g) was dissolved with 50 mL of ethanol under sonication in a centrifuge tube. Rifampin (0.328 g) was dissolved in 20 mL of dichloromethane under sonication in a centrifuge tube. The silicone elastomer MED-6215 Part A (72.2 g) was weighed into a clear plastic jar. The jar was secured to a mixer stand and mechanical mixer propellers were inserted. The speed of the mixture unit was adjusted to 6 and the solution of rifampin in dichloromethane was added slowly by pipette. Next, the solution of minocycline in ethanol was added slowly by pipette. Following addition of the drug solutions, nitrogen gas (1-5 PSI) was directed into the mixing silicone to aid in evaporation of solvents. The silicone mixture was allowed to mix for 1-4 hours to evaporate solvents. MED-6215 Part B (7.2 g) was weighed into a 50 mL beaker, added to the mixing solution of minocycline, rifampin and MED-6215 Part A, and allowed to mix for an additional 10 minutes. The mixture was de-gassed under a bell jar with a vacuum pump until bubbling stopped. Using a 10 mL plastic syringe, a desired volume of the mixture was extracted and injected into the appropriate mold (after applying a small amount of silicone mold release). The mold was placed in an oven at 70° C. for a minimum of 20 minutes. The directly incorporated silicone elastomer product was obtained following removal of the mold from oven and removal of the cured silicone part from the mold.

Inhibition of Biofilm Formation

Inhibition of biofilm formation was tested using levofloxacin or ciprofloxacin directly incorporated into a 14 cm long 50 A durometer silicone tube (14 Fr). The effects of directly incorporated levofloxacin and ciprofloxacin were compared with an 80 A durometer silicone tube with no drug and a Spectrum® Foley catheter. The direct-incorporated tubes were subjected to a continuous one-way flow of sterile filtered artificial urine media (1 mL/min) for one, two, or three days. For elution, the tubing was inserted into a longer length of 4.8 mm inner diameter tubing allowing the urine media to flow both intralumenally and extralumenally. All tubing used in the flow apparatus was sterilized prior to use. At each time point, one test article was removed from the elution apparatus as aseptically as possible and a 4 cm long piece was cut off for HPLC testing. The remaining length was placed into a sterile container and frozen at −20° C. until ready for biofilm testing.

In preparation for biofilm testing, the articles were thawed, sectioned into 1 cm pieces, and mounted on stainless steel pegs to facilitate handling during the assay. Pieces were placed individually in 13 mm×100 mm glass test tubes and challenged with 3 mL of trypticase soy broth containing approximately 500,000 colony forming units (CFU) of the selected microbial species (i.e., 1.67×105 CFU/mL). Articles were evaluated in triplicate per species per time point when sufficient test article length was available. Once inoculated, tubes were aerobically incubated at 36° C. (±1° C.) for 18-20 hours, at which time adhered bacteria were enumerated.

Enumeration involved removing the pegged test article pieces from the glass culture tubes and placing them into clean 15 mL conical tubes containing 10 mL of saline to wash off unattached bacteria. The wash tubes were placed vertically in an orbital shaker incubator set at 100 RPM and 37° C. for 10 minutes. After washing, the test article pieces were removed from the stainless steel pegs and placed in new 15 mL conical tubes containing 5 mL of saline. Adhered bacteria were dislodged from test article pieces via sonication for 15 minutes at room temperature followed by 20 seconds of vortexing. Dislodged bacteria were then serially diluted and drop plated on trypticase soy agar plates and incubated aerobically at 36° C. CFU on drop plates were counted 15-18 hours later and the CFU per centimeter of test article calculated.

Table 2 shows the test data for direct-incorporated silicone tubes at days 0, 1, 2, and 3 compared with a Spectrum® Foley catheter and a control 80 A silicone tube. The data are expressed as the mean $\log_{10}$ CFU/cm.

TABLE 2

| | Inhibition of Biofilm Formation[a] | | | | |
|---|---|---|---|---|---|
| | Test Article | Day 0 | Day 1 | Day 2 | Day 3 |
| E. faecalis | 80A silicone-no drug | 6.91 ± 0.33 | NT | NT | NT |
| | Spectrum ® Foley | 3.09 ± 0.12 | 3.40 ± 0.35 | 2.67 ± 0.55 | 3.82 ± 0.25 |
| | Levofloxacin[b] | 0.00 | 1.07 ± 1.85 | 1.28 ± 1.24 | 2.68 ± 0.46 |
| | Ciprofloxacin[b] | 0.57 ± 0.98 | 0.00 | 0.00 | 0.94 ± 1.62 |
| | Levofloxacin[c] | NT | 0.73 ± 1.26 | 0.37[a] | 0.56 ± 0.98 |

TABLE 2-continued

| | | Inhibition of Biofilm Formation[a] | | | |
|---|---|---|---|---|---|
| | Test Article | Day 0 | Day 1 | Day 2 | Day 3 |
| P. aeruginosa | 80A silicone-no drug | 6.69 ± 0.25 | NT | NT | NT |
| | Spectrum ® Foley | 4.37 ± 0.29 | 5.28 ± 0.52 | 7.77 ± 0.67 | 6.82 ± 0.77 |
| | Levofloxacin[b] | 0.00 | 0.00 | 0.96 ± 1.66 | 1.30 ± 2.25 |
| | Ciprofloxacin[b] | 0.00 | 0.00 | 0.00 | 0.00 |
| | Levofloxacin[c] | NT | 1.37 ± 2.38 | 0.57 ± 0.98 | 1.21 ± 2.10 |

[a]Data are in mean $\log_{10}$CFU/cm with standard deviations.
[b]50A durometer silicone made from high-consistency elastomer NuSil MED-4050.
[c]50A durometer silicone from a low-consistency elastomer.

Drug Elution Rates

Samples of tubing (4 cm) were taken at each day of the biofilm study to determine the amount of drug remaining in the silicone tubes after continuous exposure to artificial urine for zero to three days. The 4 cm pieces of tubing were soaked in an appropriate organic solvent (e.g., dichloromethane) to extract the drug from the tube and a solvent aliquot analyzed by HPLC to determine the amount of drug remaining per gram of silicone tube. Table 3 shows the amount of drug remaining in the silicone tubes at each time point, with the data expressed in mg of drug per gram of silicone.

TABLE 3

| | Drug Elution Rates[a] | | | |
|---|---|---|---|---|
| | Day No. | | | |
| Drug | 0 | 1 | 2 | 3 |
| Minocycline-Spectrum ® (impregnated) | 0.58 | 0.41 | 0.25 | 0.042 |
| Rifampin-Spectrum ® (impregnated) | 0.59 | 0.53 | 0.53 | 0.43 |
| Levofloxacin[b] | 14.6 | 13.6 | 13.4 | 13.3 |
| Ciprofloxacin[b] | 18.7 | 17.5 | 17.0 | 16.3 |
| Levofloxacin[c] | 18.3 | 18.0 | 18.4 | 18.4 |

[a]Data in mg/g.
[b]50A durometer silicone made from high-consistency elastomer NuSil MED-4050.
[c]50A durometer silicone from a low-consistency elastomer.

Although Table 3 shows elution data for silicones directly incorporated with a single drug, multiple drug elution may occur where more than one drug has been incorporated into the silicone body.

Zone of Inhibition (ZOI) Test

Antimicrobial activity can also be measured using a Zone of Inhibition (ZOI) test, also known as the Kirby-Bauer test. A microbial suspension is first spread with a sterile swab, evenly, over the face of a sterile agar plate. Next, an antimicrobial test article is placed in the center of the agar plate and incubated for about 16-20 hours. If substantial antimicrobial activity is present, then a zone of inhibition appears around the test article that is free from microbial growth. A larger zone of inhibition indicates greater antimicrobial activity.

Table 4 shows results from ZOI tests with silicone tubes directly incorporated with the indicated drug or drugs. Test articles were exposed to artificial urine solution for the indicated number of days, rinsed, and then placed in the agar plate. The ZOI data is expressed as mm of inhibited microbial growth. A control tube lacking incorporated drug shows no microbial inhibition.

TABLE 4

| | Zone of Inhibition (ZOI) Test[a] | | | | | | | | |
|---|---|---|---|---|---|---|---|---|---|
| Silicone | | E. coli Test day | | | | C. albicans Test day | | | |
| type | Drug (s) | 0 | 1 | 2 | 3 | 0 | 1 | 2 | 3 |
| A | Minocycline (26 mg/g)-Fluconazole (4 mg/g) | 21 | 17 | 20 | 17 | 21 | 16 | 15 | 18 |
| B | Levofloxacin (20 mg/g)-Fluconazole (2 mg/g) | 39 | | | | 0 | | | |
| B | Ciprofloxacin (20 mg/g)-Fluconazole (2 mg/g) | 29 | | | | 0 | | | |
| B | Levofloxacin (20 mg/g)-Itraconazole (4 mg/g) | 35 | | | | 12 | | | |
| B | Gentian violet (4 mg/g)-Ciprofloxacin (20 mg/g) | 39 | 34 | 34 | NT | 23 | 15 | 15 | NT |
| C | Gentian violet (1 mg/g)-Ciprofloxacin (20 mg/g) | 33 | | | | 19 | | | |
| B | Triclosan (20 mg/g)-Fluconazole (2 mg/g) | 23 | 22 | 21 | | 17 | 16 | 17 | |
| B | Triclosan (20 mg/g)-Itraconazole (2 mg/g) | 24 | | | | 13 | | | |
| B | Trimethoprim (5 mg/g)-Levofloxacin (4 mg/g) | 27 | 22 | 21 | | 0 | 0 | 0 | |
| B | Ciprofloxacin (20 mg/g) | 36 | 34 | 32 | 29 | 0 | 0 | 0 | 0 |
| C | Ciprofloxacin (20 mg/g) | 38 | 28 | 33 | 33 | 0 | 0 | 0 | 0 |
| C | Minocycline HCl (20 mg/g) | 23 | 18 | 18 | 16 | 12 | 11 | 9 | 9 |
| B | Triclosan (2 mg/g) | 17 | | | | 0 | | | |
| B | Triclosan (5 mg/g) | 21 | | | | 9 | | | |
| B | Triclosan (10 mg/g) | 25 | | | | 13 | | | |
| B | Triclosan (20 mg/g) | 26 | 23 | 23 | | 15 | 13 | 14 | |
| B | Levofloxacin (5 mg/g) | 25 | | | | 0 | | | |
| B | Levofloxacin (20 mg/g) | 27 | 26 | 27 | | 0 | 0 | 0 | |
| C | Levofloxacin (20 mg/g) | 36 | 35 | 31 | 27 | 0 | 0 | 0 | 0 |
| B | Trimethoprim (12 mg/g) | 11 | 8 | 9 | | 0 | 0 | 0 | |
| B | Flucytosine (2 mg/g) | NT | | | | 10 | | | |
| B | Itraconazole (2 mg/g) | NT | | | | 17 | | | |
| B | Itraconazole (6 mg/g) | NT | | | | 18 | | | |
| B | Gentian violet (4 mg/g) | 9 | 0 | 0 | NT | 22 | 18 | 14 | NT |

[a]Data expressed in mm.
A = 50A durometer silicone made from low-consistency elastomer NuSil MED-6215.
B = 50A durometer silicone.
C = 50A durometer silicone made from high-consistency elastomer NuSil MED-4050.

The foregoing description of the invention has been presented for purposes of illustration and description, and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated.

What is claimed is:

1. An antimicrobial barrier device comprising:
a soft durometer cured silicone body having 10 A to about 80 A durometer, being greater in width (L1) than thickness (L2), and having an outer edge, the soft durometer cured silicone body comprising one or more directly incorporated antimicrobial drugs selected from the group consisting of an antifungal agent and an antibacterial agent, the soft durometer cured silicone body being substantially resistant to microbial colonization thereon, and having
   a) a first surface adapted to conform to a treatment area;
   b) a hole extending therethrough, the hole being adapted to receive and seal to an insertable medical device, the size of the hole being equal to or smaller than the circumference of the insertable medical device, the hole having a shape selected from the group consisting of substantially round or rounded, scalloped oval, and eclipse;
   c) an outer edge; and
   d) at least one of an adhesive, tape, bandages, ties, sutures, or straps for adhering the first surface to the treatment area;
   wherein the antimicrobial barrier device inhibits bacterial growth in a zone of inhibition of about 10 mm to 30 mm from the outer edge.

2. The antimicrobial barrier device of claim 1 wherein the soft durometer cured silicone body is 10 A to about 50 A durometer silicone.

3. The antimicrobial barrier device of claim 1 wherein the soft durometer cured silicone body is about 50 A durometer silicone.

4. The antimicrobial barrier device of claim 1 wherein the one or more directly incorporated antimicrobial drugs is selected from the group consisting of a rifamycin, rifampicin, nitrofurantoin, triclosan, trimethoprim, nalidixic acid, vancomycin, a tetracycline, doxycycline, minocycline, tetracycline, an aminoglycoside, amikacin, gentamicin, neomycin, tobramycin, a fluoroquinolone, ciprofloxacin, levofloxacin, trovafloxacin, gemifloxacin, gentian violet, flucytosine, an azole drug, fluconazole, miconazole, itraconazole, ketoconazole, clotrimazole, and chlorhexidine.

5. The antimicrobial barrier device of claim 4 wherein the one or more directly incorporated antimicrobial drugs is directly incorporated in a concentration of about 1 mg to about 30 mg per gram of soft durometer cured silicone body.

6. The antimicrobial barrier device of claim 1 wherein the one or more directly incorporated antimicrobial drugs is directly incorporated in a concentration in mg per gram of soft durometer cured silicone body, wherein the directly incorporated antimicrobial drugs and concentrations are:
   a) about 10 mg/g to about 20 mg/g ciprofloxacin;
   b) about 4 mg/g to about 20 mg/g levofloxacin;
   c) about 20 mg/g to about 30 mg/g minocycline;
   d) about 10 mg/g to about 20 mg/g triclosan;
   e) about 10 mg/g to about 20 mg/g trimethoprim;
   f) about 1 mg/g to about 6 mg/g fluconazole;
   g) about 1 mg/g to about 6 mg/g itraconazole; or
   h) about 1 mg/g to about 6 mg/g gentian violet.

7. The antimicrobial barrier device of claim 1 wherein the one or more directly incorporated antimicrobial drugs is one or more antibacterial drugs and one or more antifungal drugs, each directly incorporated in a concentration in mg per gram of soft durometer cured silicone body, wherein the antibacterial drugs and concentrations are:
   a) about 10 mg/g to about 20 mg/g ciprofloxacin;
   b) about 4 mg/g to about 20 mg/g levofloxacin;
   c) about 20 mg/g to about 30 mg/g minocycline;
   d) about 10 mg/g to about 20 mg/g triclosan; or
   e) about 10 mg/g to about 20 mg/g trimethoprim;
   and wherein the antifungal drugs and concentrations are
   f) about 1 mg/g to about 6 mg/g fluconazole;
   g) about 1 mg/g to about 6 mg/g itraconazole; or
   h) about 1 mg/g to about 6 mg/g gentian violet.

8. The antimicrobial barrier device of claim 1, wherein an adhesive is coated onto the first surface.

9. The antimicrobial barrier device of claim 8 further comprising a cover, the cover being removably attached to the adhesive.

10. The antimicrobial barrier device of claim 6, wherein the cured silicone body elutes the one or more directly incorporated antimicrobial drugs when contacted with the treatment area.

11. The antimicrobial barrier device of claim 1, wherein the soft durometer cured silicone body comprises about 1 mg/g to about 30 mg/g of the one or more directly incorporated antimicrobial drugs, wherein the soft durometer cured silicone body:
   a) is about 50 A durometer silicone;
   b) elutes about 1% to about 15% of the one or more directly incorporated antimicrobial drugs after exposure to artificial urine for about 1-3 days, and
   c) inhibits at least about 80% biofilm formation thereon.

12. The antimicrobial barrier device of claim 1, wherein the soft durometer cured silicone body comprises about 1 mg/g to about 30 mg/g of the one or more directly incorporated antimicrobial drugs, wherein the soft durometer cured silicone body:
   a) is about 50 A durometer silicone;
   b) elutes about 1% to about 15% of the one or more directly incorporated antimicrobial drugs after exposure to artificial urine for about 1-3 days, and
   c) inhibits substantially all biofilm formation thereon.

13. The antimicrobial barrier device of claim 1 further comprising a slit.

14. A kit comprising:
   an insertable medical device; and
   the antimicrobial barrier device of claim 1.

15. The kit of claim 14 wherein the insertable medical device is a catheter, a needle, an infusion device, a peripheral venous catheter, a peripheral venous catheter needle, an indwelling infusion needle, a butterfly needle, a subcutaneous access device, an insulin pump needle, a patient controlled analgesia pump needle, an arterial catheter, a central venous catheter, a dialysis catheter, a peritoneal dialysis catheter, a nephrostomy catheter, a percutaneous cystostomy catheter, an indwelling paracentesis or pleurocentesis catheter or drain, a percutaneous nephrostomy, a cystostomy tube, a spinal or epidural catheter or a sensor.

16. A method of manufacturing the antimicrobial barrier device of claim 1 by directly incorporating an antimicrobial drug into a soft durometer cured silicone body comprising the steps of:
   a) dissolving one or more antimicrobial drugs in one or more solvents to provide a dissolved one or more antimicrobial drugs;
   b) mixing the dissolved one or more antimicrobial drugs with a first silicone elastomer to provide a first silicone elastomer mixture;
   c) evaporation of the one or more solvents from the first silicone elastomer mixture to provide a second silicone elastomer mixture;
   d) mixing the second silicone elastomer mixture with a second silicone elastomer to provide a third silicone elastomer mixture;
   e) transferring the third silicone elastomer mixture to a mold; and
   f) curing the third silicone elastomer mixture in the mold.

17. The method of claim 16, wherein the first, second, and third silicone elastomer mixtures are homogeneous mixtures.

18. The method of claim 17, wherein the antimicrobial drug is selected from the group consisting of a rifamycin, rifampicin, nitrofurantoin, triclosan, trimethoprim, nalidixic acid, vancomycin, a tetracycline, doxycycline, minocycline, tetracycline, an aminoglycoside, amikacin, gentamicin, neomycin, tobramycin, a fluoroquinolone, ciprofloxacin, levofloxacin, trovafloxacin, gemifloxacin, gentian violet, flucytosine, an azole drug, fluconazole, miconazole, itraconazole, ketoconazole, clotrimazole, and chlorhexidine.

19. An antimicrobial barrier device comprising:
a soft durometer cured silicone body being greater in width (L1) than thickness (L2), having an outer edge, and comprising one or more directly incorporated antimicrobial drugs selected from the group consisting of an antifungal agent and an antibacterial agent, the soft durometer cured silicone body being substantially resistant to microbial colonization thereon, and having
a) a first surface adapted to conform to a treatment area;
b) a hole extending therethrough, the hole being adapted to receive and seal to an insertable medical device, the size of the hole being equal to or smaller than the circumference of the insertable medical device, the hole having a shape selected from the group consisting of substantially round or rounded, scalloped oval, and eclipse;
c) an outer edge; and
d) at least one of an adhesive, tape, bandages, ties, sutures, or straps for adhering the first surface to the treatment area;
wherein the one or more directly incorporated antimicrobial drugs is selected from the group consisting of a rifamycin, rifampicin, nitrofurantoin, trimethoprim, nalidixic acid, vancomycin, a tetracycline, doxycycline, minocycline, tetracycline, an aminoglycoside, amikacin, gentamicin, neomycin, tobramycin, a fluoroquinolone, ciprofloxacin, levofloxacin, trovafloxacin, gemifloxacin, flucytosine, an azole drug, fluconazole, miconazole, itraconazole, ketoconazole, clotrimazole, and chlorhexidine, and
wherein the antimicrobial barrier device inhibits bacterial growth in a zone of inhibition of about 10 mm to 30 mm from the outer edge.

20. The antimicrobial barrier device of claim 8, further comprising a peel-away layer applied over the adhesive.

* * * * *